United States Patent [19]
Lindahl et al.

[11] Patent Number: 5,776,697
[45] Date of Patent: Jul. 7, 1998

[54] CHARACTERIZATION OR DETERMINATION OF THE AMOUNT OF BLOOD CELLS BY MEANS OF POULTRY ANTIBODIES

[76] Inventors: Tomas Lindahl, S-528, 63 Linköping; Anders Larsson, S-752, 30 Uppsala, both of Sweden

[21] Appl. No.: 167,877

[22] PCT Filed: Jun. 22, 1992

[86] PCT No.: PCT/SE92/00451

§ 371 Date: Feb. 7, 1994

§ 102(e) Date: Feb. 7, 1994

[87] PCT Pub. No.: WO93/00585

PCT Pub. Date: Jan. 7, 1993

[30] Foreign Application Priority Data

Jun. 28, 1991 [SE] Sweden ................................ 9102014

[51] Int. Cl.$^6$ ........................................................ G01N 33/53
[52] U.S. Cl. ........................... 435/7.1; 435/7.2; 435/7.24; 436/52; 436/512; 436/518
[58] Field of Search ................................ 435/7.21, 7.24, 435/7.1, 7.2; 436/512, 52, 518

[56] References Cited

U.S. PATENT DOCUMENTS

| | | | |
|---|---|---|---|
| 4,357,272 | 11/1982 | Polson et al. | 530/387.1 |
| 4,474,893 | 10/1984 | Reading | 436/547 |
| 4,820,505 | 4/1989 | Ginsberg et al. | |
| 5,049,502 | 9/1991 | Humphries | 435/240.2 |

FOREIGN PATENT DOCUMENTS

0 267 886   5/1988   European Pat. Off. .

OTHER PUBLICATIONS

Dialog International Services, File 155, Medline, Dialog Assession No. 04533577. Haegert DG et al., "Test Systems for Detection of Human T Associated Ig-related Surface Determinants Using Chicken Antiglobulin Reagents", J. Immunol Methods , 1981, 46(2) pp. 65–75.

Clin. Chem., vol. 37, Nov. 3, 1991, pp. 411–414, Anders Larsson et al., "Use of Chicken Antibodies In Enzyme Immunoassays to Avoid Interference by Rheumatoid Factors".

Larsson, A. et al., "Platelet Activation and Binding of Complement Components to Platelets Induced by Immune Complexes", Platelets 5:149–155, 1994.

Hädge, D. & Ambrosius, H. "Radioimmunochemical Studies on 7.8S & 5.7S Duck Immunoglobulins in comparison with Fab & Fc fragments of Chicken IgY", Developmental and Comparitive Immunology 8(6):131–139, 1984.

Herzenberg, L. A. & Herzenberg L. A. "Analysis & separation using the fluorescence–activated cell sorter (FACS)"in: Handbook of Experimental Immunology , vol. 2, D. M. Weir, ed. Oxford: Blackwell Scientific Publications, 1978.

Lindahl L. et al., "Studies of Fibrinogen Binding to Platelets by Flow Cytometry: An Improved Method for Studies of Platelet Activation", Thrombosis & Haemostasis 68(2): 221–225, 1992.

Warkentin T E et al. "Measurement of fibrinogen binding to platelets in whole blood by flow cytometry: a micromethod for the detection of platelet activation". British Journal of Haematology 76: 387–394, 1990.

Larsson, A. & Sjoquist, J. "Chicken IgY: Utilizing the Evolutionary Difference". Comp. Immun. Microbiol. Infect. Dis 13(4):199–201, 1990.

Winchester R. S. & Ross G. D. "Methods for Enumerating Cell Populations by Surface Markers with Conventional Microscopy". In: Manual of Clinical Laboratory Immunology , 3rd ed. , N. R. Rose et al., eds, Washington, D. C., American Society for Microbiology, 1986, pp. 212–225.

*Primary Examiner*—Jeffrey Stucker
*Attorney, Agent, or Firm*—Burns, Doane, Swecker & Mathis, LLP

[57] ABSTRACT

A process for detection of blood cells in activated form and/or determination of a proportion of activated blood cells which comprises performing said detection and/or determination with bird antibodies, whereby interfering interactions which change expression of antigen on a surface of blood cells are eliminated.

17 Claims, 1 Drawing Sheet

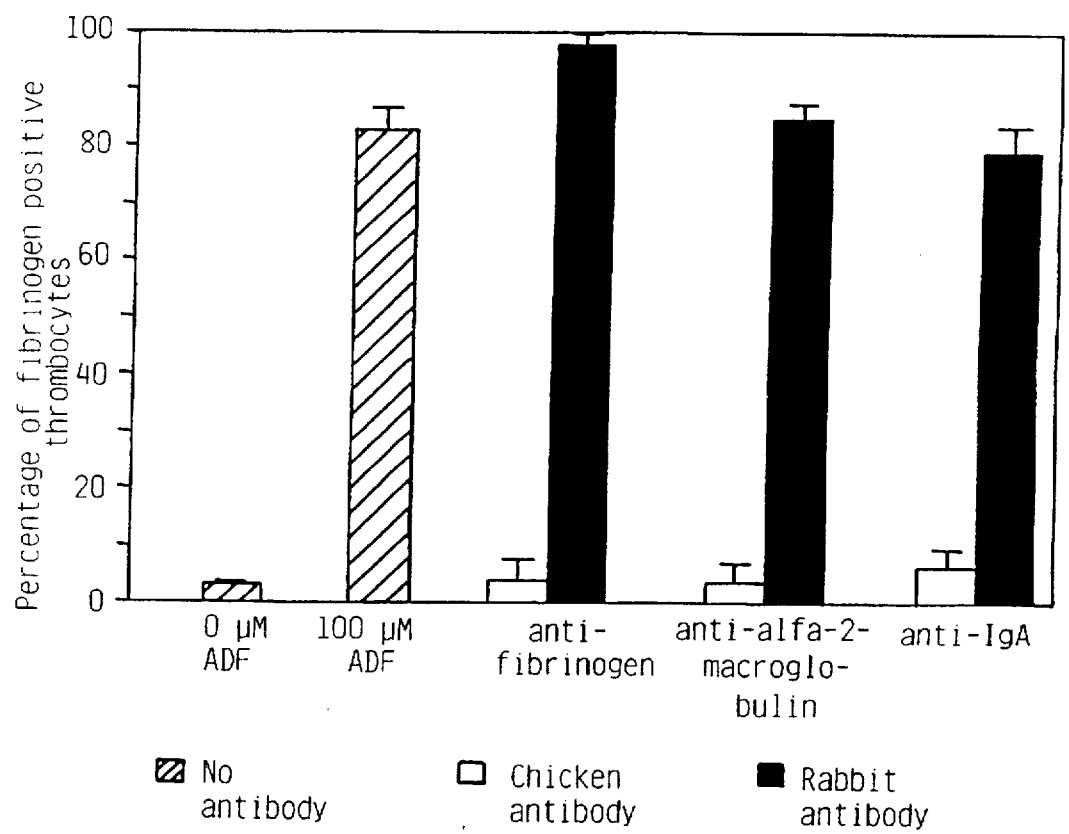

CHARACTERIZATION OR DETERMINATION OF THE AMOUNT OF BLOOD CELLS BY MEANS OF POULTRY ANTIBODIES

TECHNICAL FIELD

The present invention relates to a process for the characterization or determination of the amount of mammalian cells according to the technique previously known per se where antibodies are utilized for said purpose. Up to now antibodies prepared in a mammal, especially rabbit, have been utilized for such purposes, but the present invention relates to the utilization of other types of antibodies in these connections, whereby disadvantages in connection with the prior art are eliminated, even in such a way that the invention enables such characterizations or determinations which would otherwise be troublesome or even impossible.

BACKGROUND OF THE INVENTION

Although the invention is generally applicable to the characterization or determination of many different types of mammalian cells, which will be more specifically exemplified below, it is of a very great value in connection with thrombocytes (blood platelets), especially with reference to the central parts of the thrombocyte functions in different connections. Therefore, a background of the invention will be given with reference to thrombocytes, as the problems to be solved by the invention and the advantages thereof will be most obvious thereby. However, corresponding or similar advantages can be achieved in the determination of other mammalian cells.

Thrombocytes have a central part of the haemostasis. It is well known that low thrombocyte numbers in the blood give rise to bleeding complications. There are also data which indicate that an increased number of activated thrombocytes and/or a reduced activation threshold may have an importance for the development of thrombi. Also such diseases as preeclampsia (a syndrome of pregnants with the symptoms of high blood pressure and urine protein) are associated with such alterations of the normal thrombocyte functions. Examinations of the thrombocyte functions can also be expected to become of great importance for decisions as to which patients should receive thrombocyte concentrates.

Haemostasis requires aggregation of thrombocytes. However, said aggregation can take place only if the thrombocytes will expose receptors for fibrinogen on their surfaces. In their condition of rest the thrombocytes have a minor capability of binding fibrinogen and then they can not either form aggregates which are the primary haemostatic plug (the first blocking of a vascular lesion) or part of a thrombosis (a clot). The activation of thrombocytes means that the thrombocytes will get a significantly increased capability of binding fibrinogen.

In other words there is a great demand of determining, in the blood of a patient, the amount or portion of the thrombocytes which are activated, i.e. which are highly capable of binding fibrinogen. However, those routine methods which have been utilized for testing the thrombocyte function, e.g. bleeding time and thrombocyte aggregation, are complex and insensitive and merely give a non-specific information about the function. For instance, they will give no picture of the discrete or separate thrombocytes but merely an average value. Furthermore, there are methods for determining proteins which are liberated from the thrombocytes, but the results thereof are unreliable as they are influenced inter alia by the metabolism of the patient.

In recent years fluorescence activated flow cytometry has, however, made it possible to develop new assays of thrombocyte functions. In this context laser beams are utilized which illuminate cells in a passing liquid jet. The light scattering gives information about the sizes of the cells and their structures. Further information will be obtained by the addition of antibodies or other substances which have been linked to different substances which when illuminated are caused to produce light (fluorescence). These methods are rapid and sensitive and can give a specific information about thrombocyte functions. Moreover, it is possible to study each thrombocyte separately and not only an average of all thrombocytes. For an assay a few microliters of whole blood or thrombocyte-rich plasma will be required. The thrombocytes can be differentiated from other blood cells by means of a specific antibody or by their sizes.

Commercially available fluorescence-labelled rabbit antibodies have been utilized for the study of the fibrinogen binding of thrombocytes in these connections. This is disclosed in an article by R. M. Hardisty et al. in "Measurement of fibrinogen binding to platelets in whole blood by flow cytometry: a micro method for the detection of platelet activation." Br. J. Hematol 1990, 76, 387–394.

GENERAL DISCLOSURE OF THE INVENTION

According to the present invention it has unexpectedly been shown that by the choice of another kind or type of antibodies than those mammalian antibodies which have previously been utilized for the characterization or determination of mammalian cells, essential advantages are achieved relative to the prior art.

More specifically it has been found that by selecting antibodies from birds or reptiles one can avoid or eliminate method artefact appearing in connection with mammalian antibodies. Thus, mammalian antibodies form immuno complexes with fibrinogen in plasma, which activate the thrombocytes and give rise to erroneous assay results. Apparently this is not all or to a very reduced extent the case when utilizing the novel antibodies according to the present invention. Although the invention is not limited to any specific theory in this context, it seems as if the antibodies from birds and reptiles do not provoke physiological reactions in the formation of complexes with antigen and interactions with antibody-specific cell receptors.

In other words the present invention is based on the unexpected discovery that in experiments with antibodies against fibrinogen, which antibodies had been prepared by the immunization of hens with human fibrinogen, fibrinogen could be found on the thrombocyte surfaces without any activations of the thrombocytes, and this in spite of the fact that immuno complexes could be observed between plasma fibrinogen and fluorescence-labelled hen antifibrinogen antibody (in the experiments thrombocytes and immuno complexes could be distinguished from each other due to different light scatterings or by means of a thrombocyte antibody labelled in any other way, e.g. with another dye or with a radionucleide).

The use of hen or chicken antibodies in an assay of the ELISA type is previously known per se (see e.g. Comp. Immun. Microbiol. Infect. Dis., Vol. 13, No. 4, pp 199–201, 1990) but what is unexpected in connection with the invention is, thus, that a troublesome influence upon the examined or assayed cells is avoided.

This means that the process according to the invention is intended for the characterization or determination of such cells which interact with antibodies from mammals, or with their complexes with antigen, in any other way than by means of the antigen-binding capability of the antibodies. This generally means that such cells are referred to which are able to undergo a transformation or conversion, i.e. a change of the surface structure, and where antibodies from mammals, or their complexes with antigens, induce such a transformation or conversion.

The purpose of the process according to the invention is to assay or detect in what condition or state the cells are present or to assay or determine the amount or proportion of cells in at least one of said states, method artefacts or conversions of said cells being avoided by the invention, which would otherwise give an overrated or erroneous value of the proportion of cells in either of said states or conditions.

Although the invention has been generally described above in connection with chicken or hen antibodies, it should be useful for antibodies from birds or poultry in general as well as for antibodies from reptiles. Furthermore, it is not necessary to utilize the antibodies per se, as corresponding or similar results would be obtained by immunologically similar proteins, i.e. such proteins which possess essentially the same or similar antigen-binding activity as the antibodies referred to. For instance it may be fragments of antibodies and recombinant antibodies.

More specifically this means that the process according to the invention is characterized by utilizing, as the antibodies, antibodies from birds or reptiles or immunologically similar proteins having essentially the same or similar antigen-binding activity or capability as said antibodies and by performing the characterization and/or determination on such mammalian cells which interact with antibodies from mammals, or with their complexes with antigens in any other way than by means of the antigen-binding activities of the antibodies, said characterization meaning that one detects the state or condition in which the cells are present and/or the determination meaning that one determines the number or proportion of the cells in at least one of said states or conditions.

As concerns the expression "characterization" of mammalian cells it should be interpreted in a wide sense, especially as the characterization per se can be performed in accordance with known principles, e.g. to detect certain surface structures of the cells. Thus, the invention is applicable to any characterization where the mammalian cells interact in the way described or are present in a convertible form and where the convertion could influence upon the measured values or results.

According to a preferable embodiment of the invention there are used as said bird antibodies antibodies from hens or chickens, such as from chicken blood.

Furthermore, it can often be advantageous rather to utilize hen or chicken antibodies from eggs, as the amount of antibodies thereby obtainable is considerably larger than if chicken blood were used as the source.

Especially with reference to what has been mentioned above in connection with thrombocytes it may also be preferable to utilize chicken antifibrinogen antibodies (throughout the specification and claims the term chicken is used to include also hen).

In connection with all preferable embodiments concerning chicken antibodies it should be understood that said applications also comprise uses of the corresponding immunologically similar proteins.

The process according to the invention is applicable to the characterization or determination of the amount or number of any mammalian cells, e.g. blood cells, such as thrombocytes and white blood cells, or leucocytes, or endothelial cells, etc., but for the above-mentioned reasons the characterization and/or determination of thrombocytes is of course especially interesting, the purpose generally being to detect thrombocytes in activated forms or to determine the proportion of activated thrombocytes. In this context activation primarily means the capability of binding fibrinogen.

Furthermore, it can be added that the process according to the invention is preferably performed in the form of fluorescence activated flow cytometry (FACS=Fluorescent Antibody Cell Sorter), especially with reference to the fact that said method is rapid, sensible and gives specific information.

EXAMPLES

For the purpose of comparing the invention with the use of antibodies according to prior art thrombocytes in plasma were admixed with antibodies from chicken and rabbit, respectively, directed against the human plasma proteins fibrinogen, $\alpha$-2-macroglobulin and IgA. The concentrations of said antibodies were selected in such a way that immuno complexes would be formed to a great extent. The degree of activation was measured by means of fluorescence-labelled chicken antibodies directed against fibrinogen. As a negative control there was added merely a saline and as a positive control the known thrombocyte-activating substance adenosine diphosphate.

A detailed method description will follow below and the results are presented in the accompanying figure, from which it can be gathered that a strong activation was obtained with all immuno complexes containing rabbit antibodies. On the contrary, the only combination with chicken antibodies for which an activation was obtained was in the complex with IgA, but in this specific case the human immunoglobulin IgA in itself should be responsible for said activation.

DETAILED METHOD DESCRIPTION

Reagents

Normal mouse IgG, adenosine-5-diphosphate (grade 1) and fluorescein isothiocyanate (FITC) were purchased from Sigma (St. Louis, Mo., USA). Sephedex G-25 and DEAE-Sepharose were purchased from Pharmacia (Uppsala, Sweden). Chicken antibodies, IgG-fractions purified from egg yolks, directed against human fibrinogen, human IgA, human alfa-2-macroglobulin and mouse immunoglobulin were obtained from Immunsystem AB (Uppsala, Sweden). The antifibrinogen antibodies were affinity purified on insolubilized human fibrinogen (Larson, A. et al J Immunol Meth 1988, 113:93–99). Some of these were conjugated with FITC after having been displayed during a night against 0.1 mole/L of $NaHCO_3$, pH 9.5. The conjugation ration was 11.1, i.e. 11 parts by mole of FITC per 1 part by mole of antibody. The mixture was incubated at room temperature in darkness for three hours. Conjugated antibodies were separated from free FITC by gel filtration in 0.01 mole/L of Tris, pH 7.3, by gel filtration of Sephadex G-25. Antibodies having the proper F/P-ratio were separated by means of ion exchange chromatography on DEAE-Sepharose CL 6B. The column was washed with the Tris-buffer with an addition of 0.1 mole/L of NaCl and the antibodies were eluted by means of a saline gradient to 0.25 mole/L. Non-conjugated and FITC-conjugated rabbit antibodies against human fibrinogen, human IgA, human alpha-2-macroglobulin and mouse immunoglobulin were purchased from Dakopetts AS (Glostrup, Denmark).

Blood testing

Venous blood was taken with an open needle without stasis from healthy volunteers who had not taken any medicine during the last 2 weeks.

4.5 mL of blood were collected in plastic tubes containing 0.5 mL of 3.8% sodium citrate. Thrombocyte-rich plasma was prepared by centrifugation for 10 minutes at 140 x g.

Preparation of Samples for Flow Cytometry

5 µL of thrombocyte-rich plasma were added to plastic tubes containing 50 or 55 µL of HEPES-buffer (137 mmole/L of NaCl, 2.7 mmole/L of KCl, 1 mmole/L of $MgCl_2$, 5.6 mmole/L of glucose, 1 mg/mL of bovine serum albumine and 20 mmole/L of HEPES, pH 7.40) and for some experiments 5 µL of antibodies. In some cases ADP had been added to the HEPES-buffer. The samples were carefully mixed once and were left to stand at room temperature for exactly 10 minutes. Then 10 µL of FITC-conjugated chicken antifibrinogen antibody (0.35 g/L) were added and the test tubes were left to stand for additionally exactly 20 minutes. The reaction was terminated by 500 µL of icecold PBS with or without 1% of paraformaldehyde. No washing steps were needed. The samples were kept in darkness on ice until they were analyzed in the flow cytometer, which was always performed during the same day.

Flow cytometry

The fluorescence-labelled thrombocytes in the buffer were assayed by means of a FACScan cytometer (Becton Dickinson, Mt. View, Calif., USA) equipped with a 15 mW air cooled 488 nm argon laser with light scattering forwardly (FwSc) and laterally (SSc), and green (FITC)- and red (PHYCO)-signals were collected with a logarithmic amplification with one 530/30 nm and one 585/42 nm filter for a green and red signal, respectively. Collections from 10,000 cells per sample and computer processings thereof were made with a Consort 30 program (also Becton Dickinson) on a Hewlett Packard 310 PC. Based on the light scattering properties each cell was represented by a dot in a rectangular system of coordinates. A collection window is placed around the crowd of dots representing the thrombocytes. Controls have been made with fluorescence-labelled antibodies against the thrombocyte receptors GPIIIa and GPIb. The instrument gives the percentage of positive cells (for fibrinogen generally thrombocytes in a buffer with the addition of adenosine and theophyllamine or EDTA have been chosen as the negative control, for the above-mentioned glycoproteins a fluorescence-labelled antibody against the leucocyte surface antigen CD-3), the average fluorescence intensity, the complexity (SSc) and the average particle volume (FwSc) of the cell population within the analysis window.

Other Experimental Results

The activation of immuno complexes can at least partly be counteracted if the thrombocytes are firstly mixed with a monoclonal antibody against the Fc-receptor. Immuno complexes between mouse antibodies and rabbit antibodies activate thrombocytes but not complexes between mouse antibodies and chicken anti-mouse-antibodies. At least some monoclonal antibodies against thrombocyte surface antigen may give some activation without the addition of any other antibody. Said activation is strongly enhanced by rabbit-anti-mouse-antibodies but not chicken-anti-mouse-antibodies.

We claim:

1. A process for detection of blood cells in activated form and/or determination of a proportion of activated blood cells which comprises performing said detection and/or determination with poultry antibodies, whereby intefering interactions which change expression of antigen on a surface of blood cells are eliminated.

2. A process according to claim 1 wherein said poultry antibodies are chicken antibodies.

3. A process according to claim 2 wherein said chicken antibodies are from eggs.

4. A process according to claim 3 wherein said blood cells are thrombocytes or leucocytes.

5. A process according to claim 4 wherein the poultry antibodies are chicken antifibrinogen antibodies.

6. A process according to claim 2 wherein said detection and/or determination is performed in the form of fluorescence-activated flow cytometry.

7. A process according to claim 2 wherein said blood cells are thrombocytes or leucocytes.

8. A process according to claim 3 wherein said detection and/or determination is performed in the form of fluorescence-activated flow cytometry.

9. A process according to claim 3 wherein the poultry antibodies are chicken antifibrinogen antibodies.

10. A process according to claim 1 wherein said blood cells are thrombocytes or leucocytes.

11. A process according to claim 10 wherein said blood cells are thrombocytes.

12. A process according to claim 11 wherein said detection and/or determination is performed in the form of fluorescence-activated flow cytometry.

13. A process according to claim 11 wherein the poultry antibodies are chicken antifibrinogen antibodies.

14. A process according to claim 10 wherein said detection and/or determination is performed in the form of fluorescence-activated flow cytometry.

15. A process according to claim 10 wherein the poultry antibodies are chicken antifibrinogen antibodies.

16. A process according to claim 1 wherein said detection and/or determination is performed in the form of fluorescence-activated flow cytometry.

17. A process according to claim 1 wherein the poultry antibodies are chicken antifibrinogen antibodies.

* * * * *